United States Patent [19]

Thompson

[11] Patent Number: 5,607,472
[45] Date of Patent: Mar. 4, 1997

[54] INTRAOCULAR LENS FOR RESTORING ACCOMMODATION AND ALLOWS ADJUSTMENT OF OPTICAL POWER

[75] Inventor: Keith P. Thompson, Atlanta, Ga.

[73] Assignee: Emory University, Atlanta, Ga.

[21] Appl. No.: 437,792

[22] Filed: May 9, 1995

[51] Int. Cl.⁶ ........................................ A61F 2/16
[52] U.S. Cl. .................................................... 623/6
[58] Field of Search .................................. 623/4–6

[56] References Cited

U.S. PATENT DOCUMENTS

| | | | |
|---|---|---|---|
| 4,449,257 | 5/1984 | Koeniyer | 623/6 |
| 4,883,485 | 11/1989 | Patel | 623/6 |
| 4,932,966 | 6/1990 | Christie et al. | 623/6 |
| 5,171,266 | 12/1992 | Wiley et al. | 623/6 |
| 5,266,074 | 11/1993 | Nishi et al. | 623/6 |
| 5,366,502 | 11/1994 | Patel | 623/6 |

FOREIGN PATENT DOCUMENTS

| | | | |
|---|---|---|---|
| 1168238 | 7/1985 | U.S.S.R. | 623/6 |
| 9208422 | 5/1992 | WIPO | 623/6 |

*Primary Examiner*—Mary Beth Jones
*Attorney, Agent, or Firm*—James W. Kayden; Thomas, Kayden, Horstemeyer & Risley

[57] ABSTRACT

An accommodating lens is designed to be inserted into a substantially intact capsulary bag having a capsulorexis opening in its anterior wall. The lens has an accommodating portion adapted to be affixed to the anterior wall of the capsulary bag adjacent the opening. The focal length of the deformable portion is alterable by insertion of a deforming material into the deformable portion thereof. In another embodiment, the focal length of a second deformable portion of the lens is varied by insertion or extraction of deformable material into or from the second portion.

43 Claims, 3 Drawing Sheets

RELAXED STATE   ACCOMMODATIVE STATE

RELAXED STATE     FIG. 2B     ACCOMMODATIVE STATE

INTRAOCULAR LENS FOR RESTORING ACCOMMODATION AND ALLOWS ADJUSTMENT OF OPTICAL POWER

FIELD OF INVENTION

This invention relates to intraocular lenses and, more particularly to a focusable intraocular lens that can restore accommodation for near vision.

BACKGROUND OF THE INVENTION

The normal healthy human eye is capable, by means of the ciliary muscle, of altering the focus of the crystalline lens to focus on distant objects and to focus on near objects as well. This latter capability is known as accommodation and is realized by contraction of the ciliary muscle which causes the lens to assume a more spherical shape, thereby increasing its power. As a person ages, the eye gradually loses its ability to change focus readily, and hence, its ability to accommodate, thereby forcing the individual to resort to reading glasses for close up work. This condition is termed presbyopia.

Loss of accommodation can also occur, drastically, when the crystalline lens of the eye becomes clouded or opaque, commonly referred to as cataract formation, and must be removed and replaced by a plastic or glass intraocular lens. Such intraocular lenses are usually fixed focus lenses, so that accommodation cannot be readily realized. Thus, the patient having an intraocular lens implanted in the eye must resort to corrective glasses for reading or close-up work. In addition, it has proven to be extremely difficult to achieve a desired degree of refraction in such an intraocular lens, the accuracy of achieving the desired refractive outcome following implantation having a standard deviation of approximately one (1.00) diopter. As a consequence, the majority of patients having intraocular implants must resort to spectacles to obtain their best distance vision. In some cases the postoperative refractive error is so large that removal and replacement of the intraocular lens becomes necessary.

There have been numerous attempts to achieve at least some useful degree of accommodation with an intraocular implantation which, for various reasons, fall short of being satisfactory. In U.S. Pat. No. 4,666,446 of Koziol et al., there is shown an intraocular lens having a complex shape for achieving a bi-focal result, the lens being held in place within the eye by arms, i.e., haptic supports, which are attached to the ciliary body or muscle. However, the implant requires the patient to wear spectacles for proper functioning. Another device shown in U.S. Pat. No. 4,944,082 of Richards et al., also utilizes a lens having regions of different focus, or a pair of compound lenses, which are held in place by haptics attached to the ciliary body. In this arrangement, contraction and relaxation of the ciliary muscle causes the haptics to move the lens or lenses, thereby altering the effective focal length. There are numerous other patented arrangements which utilize haptics connected to the ciliary body, or are otherwise connected thereto, such as are shown in U.S. Pat. Nos. 4,932,966 of Christie et al., U.S. Pat. No. 4,888,012 of Horne et al. and U.S. Pat. No. 4,892,543 of Turley, and rely upon the ciliary muscle to achieve the desired alteration in lens focus.

In any arrangement that is connected to the ciliary body, by haptic connection or otherwise, extensive erosion, scarring, and distortion of the ciliary body usually results. Such scarring and distortion leads to a disruption of the local architecture of the ciliary body and thus causes failure of the small forces to be transmitted to the intraocular lens. Thus, for a successful long-term implant, connection and fixation to the ciliary body is to be avoided if at all possible.

In U.S. Pat. No. 4,842,601 of Smith, there is shown an accommodating intraocular lens that is implanted into and floats within the capsular bag. The lens comprises front and rear flexible walls joined at their edges, which bear against the front and rear (anterior and posterior) inner surfaces of the capsular bag. Thus, when the zonules, the muscle strands joining the ciliary body to the capsular bag, exert a tensional pull on the circumference of the capsular bag, the bag, and hence the intraocular lens, is flattened, thereby changing the index of refraction of the lens. The implantation procedure requires that the capsular bag be intact and undamaged and that the lens itself be dimensioned to remain in place within the bag without attachment thereto. Additionally, the lens must be assembled within the capsular bag and biasing means for imparting an initial shape to the lens must be activated within the capsular bag. Such an implantation is technically quite difficult and risks damaging the capsular bag, inasmuch as most of the operations involved take place with tools which invade the bag. In addition, the Smith arrangement relies upon pressure from the anterior and posterior walls of the capsular bag to deform the lens, which requires that the lens be extremely resilient and deformable. However, the more resilient and soft the lens elements, the more difficult assembly within the capsular bag becomes.

The prior art thus discloses numerous arrangements for accommodating intraocular lenses, none of which is capable of providing an accommodating implant which does not, in one way or another, risk damage to the ciliary body or the capsular bag. In addition, while the prior art does show arrangements for imparting an initial bias or shape to the intraocular lens, in most cases the-focal length, once set, remain fixed except for the accommodation. As pointed out in the foregoing, the post operative refraction error can be as great as one diopter, or even more, necessitating the use of spectacles for the distance vision or in extreme cases, removal and replacement of the intraocular implant.

SUMMARY OF THE INVENTION

The present invention comprises an intraocular lens that can accommodate for near vision and which allows adjustment of its optical power after implantation. The invention further includes the method by which such a lens is implanted within and retained in place by the patient's eye. The implantation does not require the use of haptics or other potentially damaging support means, nor does it rely solely upon pressures exerted by both the anterior and posterior walls of the capsular bag. The structure of the lens and the method of implantation are such that any tool invasion of the capsular bag is minimized, thereby lessening any risk of damage to the bag.

The intraocular lens of the invention, in one preferred embodiment thereof, comprises an anterior accommodating portion and a posterior non-accommodating portion. The accommodating portion, comprises a molded body of a soft, compliant polymer that has a preferred modulus of elasticity and compliance and has, normally, an accommodating shape which it assumes in the absence of other forces. The non-accommodating portion preferably comprises a molded body of a standard hard polymer, or equivalent, that is frequently used in intraocular lenses. In order that the anterior portion may expand and constrict sufficiently to achieve the desired degree of accommodation, the rear wall of the anterior portion is fused to the front wall of the posterior portion in a limited central region.

The accommodating portion of the lens contains an expansion channel that extends for 360 degrees around the periphery thereof. The channel is connected via a tube extending through the posterior portion of the lens to a valve and an access port, through which the channel may be injected with a viscoelastic material. The expansion channel provides an adjustable means for altering the focal length of the soft portion of the lens by stretching the anterior, soft portion of the lens into a non-accommodating shape during implantation. Under normal operative implantation, the ciliary body is maximally relaxed, for example, where atropine treatment is used, hence the soft portion of the lens must have a non-accommodating shape during implantation.

The lens of the invention is designed to be implanted within the capsular bag with the anterior portion affixed to the edges of the capsulorexis formed circular opening in the anterior wall of the capsular bag. To this end, the periphery of the anterior portion of the lens has a recessed ledge formed thereon by peeling back a flap of the peripheral portion of the lens. In the preferred embodiment, four such flaps are formed, each encompassing an arc of approximately ninety (90) degrees. The expansion channel of the lens has been injected with the appropriate amount of viscoelastic gel. After removal of the crystalline lens by capsulorexis and phacoemulsification, for example, the lens is inserted into the capsular bag through the capsulorexis opening in the anterior wall of the bag. The lens is then positioned so that the edges of the opening in the bag rest upon the ledge, which has been coated with a pigmented bonding polymer. The leaves of the flap, the undersides of which may also be coated with a pigmented boding polymer, are then flipped over the edge of the opening in the capsular bag, thereby sandwiching the edge between the ledge and the flap. The assembly is then heated with, for example, a laser having an output wave length matching the absorption characteristics of the pigmented polymer gel so as to melt it. After the laser beam is removed, the gel cools quickly and fuses the lens to the capsular bag.

In a second preferred embodiment of the invention, the posterior portion of the lens is provided with an adjustable portion of a soft polymer such as silicon. The posterior adjustable portion has a peripheral expansion channel that may receive viscoelastic material through a separate channel from that of the anterior portion expansion channel. The "fixed" focusing power or focal length of the lens can be adjusted by injecting the viscoelastic material into the posterior channel either before, during or after implantation, which is basically the same as for the first embodiment. After implantation, the focal length of the intraocular lens can be fine tuned at any time and has the added advantage of permitting the patient to assist in the fine tuning process.

The intraocular lens of the present invention, by being attached to the anterior wall of the capsulary bag responds more readily and to a greater extent to the action of the ciliary body and the zonules inasmuch as tension applied by the zonules to the bag is also transmitted to the anterior portion of the lens, and thus, the lens does not rely solely on pressure by the anterior and posterior walls of the capsulary bag. In addition, the lens may be implanted by usual surgical techniques without invasion of the capsulary bag by tools which can cause damage thereto.

The various features and advantages of the present invention will be more readily apparent from the following detailed description, read in conjunction with the accompanying drawings.

BRIEF DESCRIPTION OF THE DRAWINGS

FIG. 2B is a plan view of the behavior of the lens of the eye shown in FIG. 2A;

DETAILED DESCRIPTION

Figure 1:
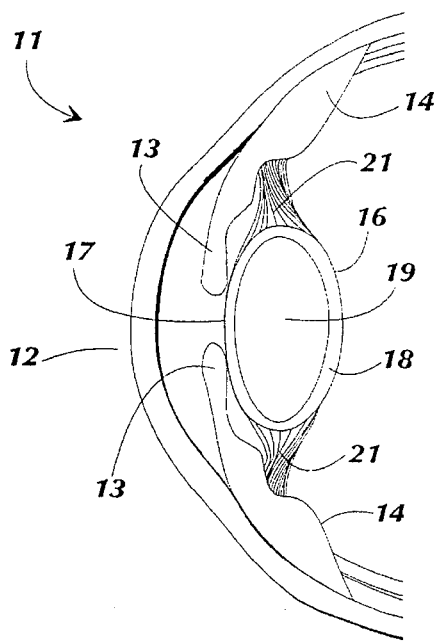
FIG. 1 is a diagrammatic cross-sectional view of a normal eye.

For a better understanding of the present invention, there is shown in FIG. 1 a diagrammatic representation of a partial cross-section of a normal human eye 11, showing those portions of the eye 11 which are involved in the practice of the present invention. The eye 11 comprises a cornea 12, an iris 13, a ciliary body 14, a capsular bag 16 having an anterior wall 17 and a posterior wall 18 and which contains a lens 19. The capsular bag 16 is connected to the ciliary body or muscle 14 by means of a plurality of strands or fibers 21, known as zonules. The ciliary body 14 surrounds the capsular bag 16 and lens 19, defining an open space, the diameter of which depends upon the state of the ciliary body 14. Thus, when the ciliary body 14 relaxes, the diameter of the opening increases, and when the ciliary body 14 contracts, the diameter of the opening decreases. When the ciliary body 14 relaxes, the zonules 21 are pulled taut and exert a radical centrifugal tensile force on the anterior 17 and posterior 18 walls of the capsular bag 19, tending to flatten it. As a consequence, lens 19 is also flattened, thereby undergoing a decrease in focusing power. This is the condition for normal distance viewing. For close up viewing, the ciliary body 14 contracts, thereby decreasing the diameter of the opening and allowing the zonules 21 to relax, which in turn removes or decreases the tension on the capsular bag 16 and allowing the lens 19 to assume a more spherical shape, increasing its focal power. Thus, it can be said that the lens 19 has a memory which causes it to assume a more rounded shape when the centrifugal forces are removed. This "memory" is in the nature of a centripetal force acting on the lens, compressing it. This increase in the focal power of the lens is accommodation, and in the normal health eye occurs automatically, by the mechanism described.

Figure 2A:
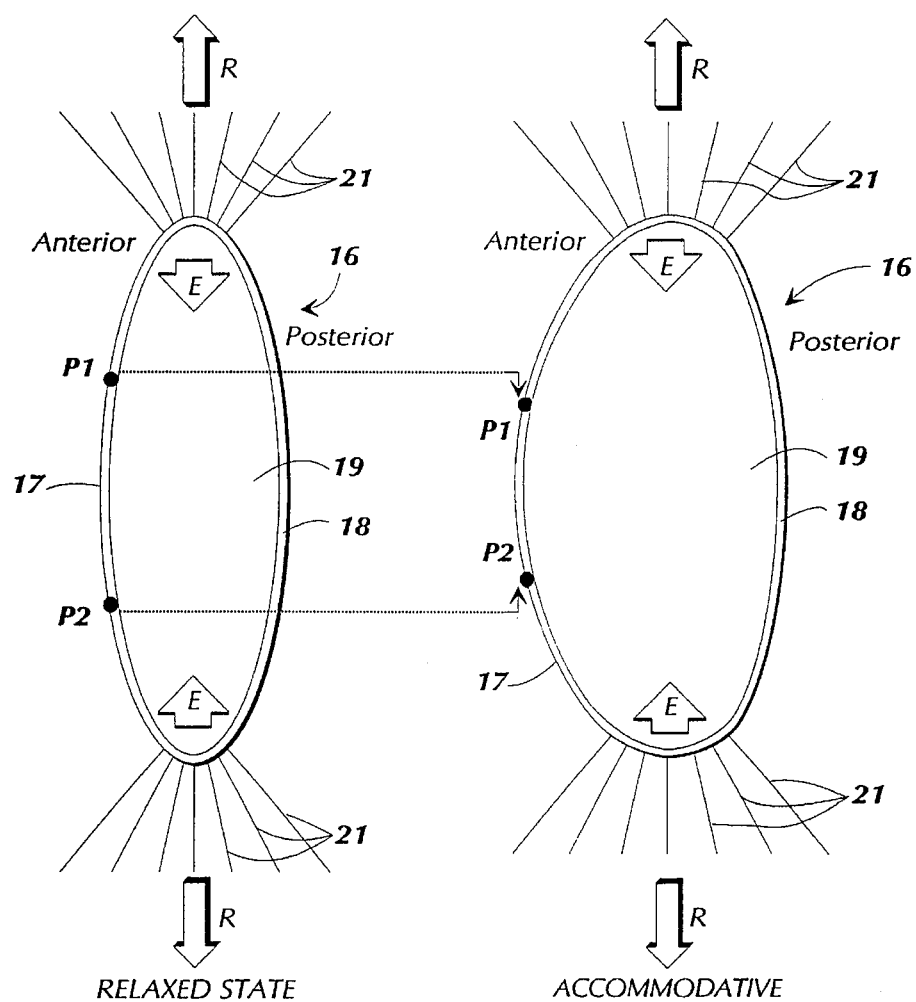
FIG. 2A is a diagrammatic view of the behavior of the lens of the eye of FIG. 1.

In FIGS. 2A and 2B the focusing phenomenon is illustrated diagrammatically. In the relaxed state of the ciliary body 14 which is shown in FIGS. 2A and 2B the centripetal forces designated by the arrows E are overcome by the centrifugal forces designated by the arrows R, and the lens 19 assumes a somewhat flattened shape, as shown, which has a particular focal length. In the accommodative state, the forces R are removed and the forces E prevail. It can be seen that the posterior wall 18 of the capsular bag does not change its shape to any great degree, but that the anterior wall 17 undergoes a marked change in shape, thereby changing its focal length. As a consequence, the distance between two spaced points P1 and P2 on the anterior wall 17 decreases as shown as accommodation takes place. In FIG. 2B, the points P1 and P2 are shown as lying on a circle 22 defined by dotted lines. It can be seen that the diameter of circle 22 is substantially less in the accommodative state than it is in the relaxed state. As will be apparent hereinafter, this phenomenon of a change in diameter is of importance in the practice of the present invention.

Figure 3A:
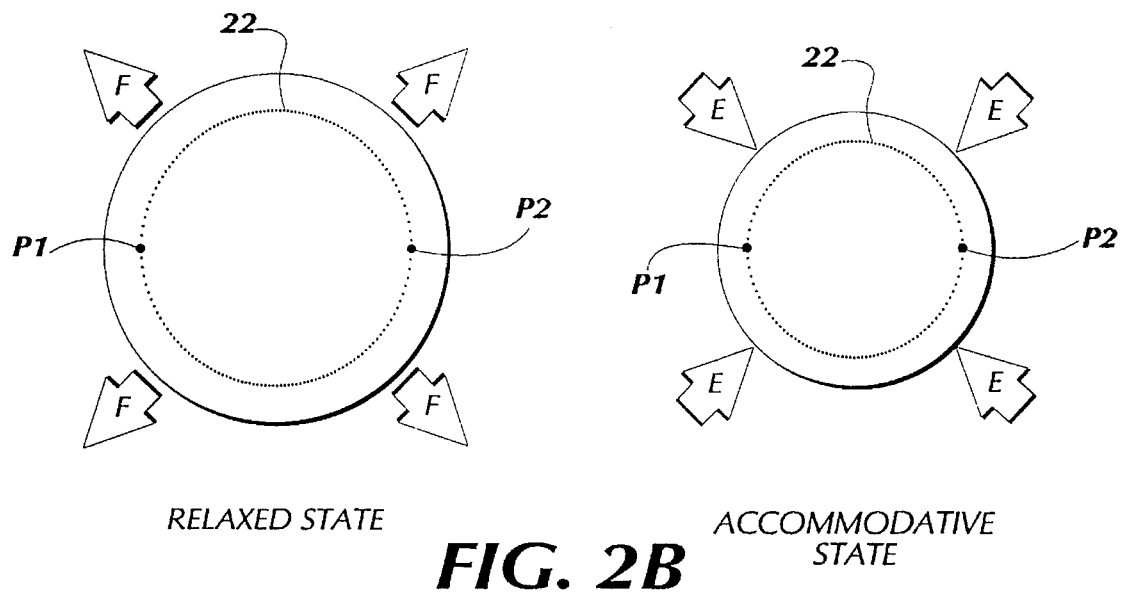
FIG. 3A is an elevation view of one embodiment of the intraocular lens of the invention.
Figure 3A:
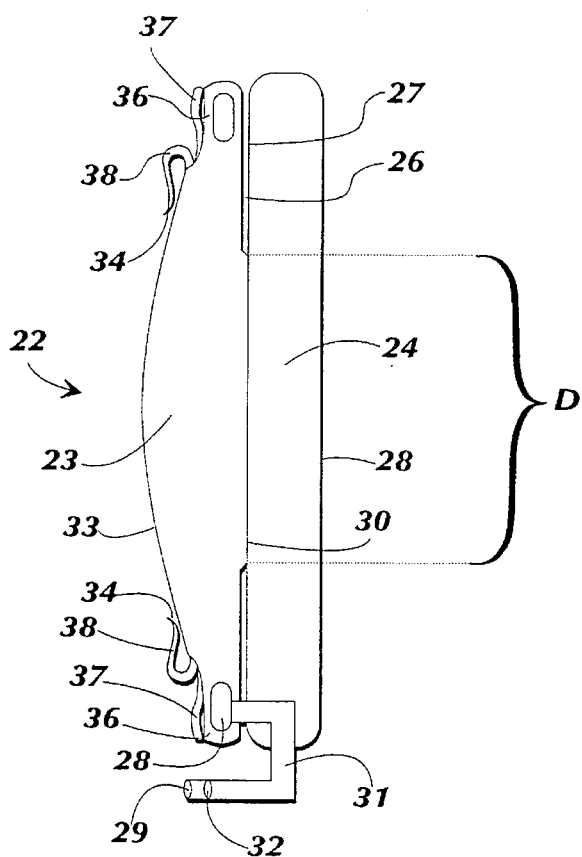
Figure 3B:
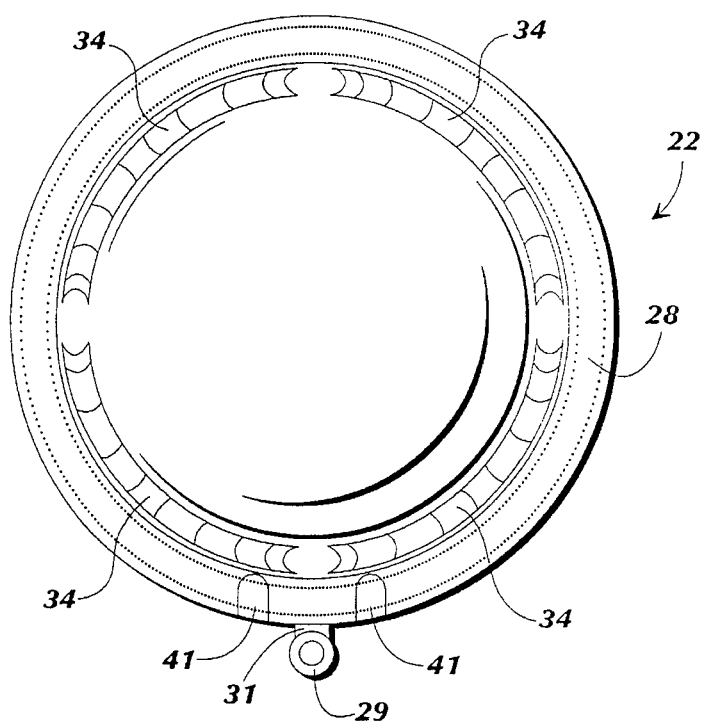
FIG. 3B is a plan view of the lens of FIG. 3A

In FIG. 3A there is shown an elevation, partially cross-sectional view of one embodiment of the present invention, and in FIG. 3B a plan view of the lens. The intraocular lens (IOL) 22 of this embodiment comprises an accommodating anterior member 23 and a non-accommodating posterior member 24 having a fixed focal length. Member 23 is made of a soft compliant polymer such as silicone having a preferred modulus of elasticity and compliance, and member 24 is composed of a standard PMMA hard polymer or equivalent that is frequently used in IOL's of conventional design. In order that the anterior member 23 be allowed to expand and contract for achieving accommodation, the rear or posterior wall 26 of member 23 is affixed, as by suitable cement or by fusing together to the front or anterior wall 27 of member 24 in a limited central area 30 having a diameter D, as shown.

Member 23 contains an expansion channel 28 that extends 360 degrees around its interior periphery, as shown in dashed lines in FIG. 3B. Channel 28 is connected to an access port through a tube 31 and a valve 32. The expansion channel 28 is designed to contain a viscoelastic material of preferred mechanical properties, which is injected into the channel 28 through access port 29. The viscoelastic material can be injected by the lens manufacturer, or by the surgeon using an appropriate injection tool. The expansion channel 28, when filled with the viscoelastic material, stretches or distorts member 23 into a "non-accommodating" shape which, as will be apparent hereinafter, is a desired condition of the lens 22 during implantation. It is to be understood that means other than an expansion channel 23 may be used to achieve the non-accommodating shape such as, for example, a circular wire and sprocket. However, the expansion channel 28 is, in most cases, the preferred means for achieving the desired result.

The anterior or front surface 33 has formed thereon a plurality of flaps 34, which extend around the periphery of member 23. As shown in FIG. 3B, there are four such flaps 34, although there may be more, if desired, as long as the flaps 34 extend around the entire periphery. The flaps 34 may be, and preferably are, formed during manufacture of the lens 22, although it is possible for the surgeon, using the proper tools, to form the flaps preferably prior to implantation. When the flaps 34 are peeled back, as shown in FIG. 3A, a peripheral recessed ledge 36 is formed, or exposed. Prior to implantation, a layer 37 of a pigmented bonding polymer of silicone or similar material is placed upon ledge 36 around the periphery thereof. It is preferable that the undersurface of the flaps 34 also be coated with a thin layer 38 of the bonding polymer, although, as will be apparent hereinafter, the layer 38 is not strictly necessary. The bonding polymer preferably has the characteristics of preferential absorption of laser light of a particular wavelength, that is outside of the absorption range of the other polymers involved in the invention. Thus, when impinged by laser light of the appropriate frequency, the bonding polymer is heated to the melting point while the remaining polymers are unaffected. Instead of a light sensitive polymer, layers 37 and 38 may comprise a bonding polymer that can be chemically activated by a chemical that does not affect the other polymers.

The lens 22 of FIGS. 3A and 3B is designed to be implanted within a substantially intact capsular bag 16 following cataract removal, for example. Cataract removal is performed in a convention manner using capsulorexis and phacoemulsification. Capsulorexis involves the cutting of a centrally located circular hole in the anterior wall 17 of the capsular bag 16. This hole, referred to as a capsulorexis, is generally approximately six millimeters (6 mm) in diameter with a tolerance of +/−0.5 mm. The dashed circle 22 in FIG. 2B represents such a capsulorexis, and reference numeral 22 is used henceforth to designate the edge of the capsulorexis. There are numerous techniques involving commercially available apparatus for forming the capsulorexis, through which the cataract impaired lens in extracted by, for example, a technique known as phacoemulsification. After the lens is removed, the capsular bag 16 is empty, but substantially intact except for the capsulorexis.

The lens 22 is prepared for insertion into the capsular bag 16 through the capsulorexis 22 by injecting the appropriate amount of viscoelastic gel through access port 29 into channel 28 to flatten the anterior lens member 23 into a non-accommodative shape. As pointed out hereinafter, such injection of the viscoelastic gel into channel 28 may be done during manufacture instead of by the surgeon. The desirability of imparting a non-accommodating shape to the member 23 stems from the fact that, during the operation, the ciliary body 14 is in a relaxed, i.e., non-accommodating state, as a result, for example, of atropine treatment during the surgery, hence the member 23 should be in the same or corresponding state. After preparation, the lens 22 is grasped by a suitable grappling instrument at the grappling points 41 and is slid into the capsular bag 16 through capsulorexis 22. The surgeon positions the lens so that the edge 22 of the capsulorexis surrounds the ledge 36, with the underside of the anterior wall 17 of capsular bag 16 resting on the ledge 36. Each of the leaver or flaps 34 is then flipped over, thereby sandwiching the wall 17 between the bonding layer 37 and the flaps 34. A conventional ophthalmic or other suitable laser having an output wavelength that matches the absorption characteristics of the pigmented polymer forming layer 37, and layer 38 if used, is used to heat the polymer, which melts briefly, then cools quickly, thereby bonding the anterior wall 17 of the bag 16 to the anterior wall of member 23, as shown in FIG. 4.

With the intraocular lens thus implanted, where it is actually part of the anterior wall 17 of capsular bag 16, the centripetal and centrifugal forces produced by the capsular bag 16, the zonules 21 and the ciliary body 14, as well as the centripetal force of the anterior portion 23 of lens 22, the shape of the portion 23 and thus its optical power are regulated by the normal anatomical changes in the ciliary body both for accommodation and distance viewing.

Figure 4:
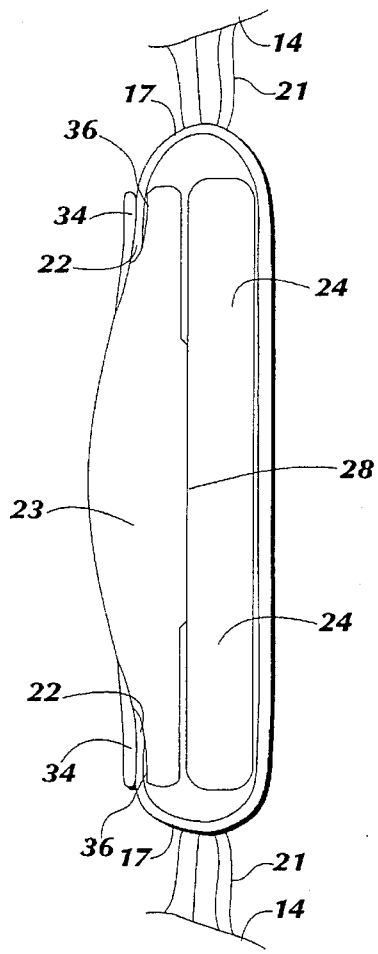
FIG. 4 is a diagrammatic cross-sectional view of an eye with the intraocular lens of FIGS. 3A and 3B implanted therein.

Inasmuch as in the IOL lens arrangement of FIG. 4, the anterior wall 33 of the accommodating portion 23 is directly attached to the periphery of the capsular bag 16, the IOL 22 of the invention responds to the normal anatomical changes in the ciliary body 14. Thus, accommodation occurs when the ciliary body 14 contracts, relieving the tension on the zonules 21, and the accommodating portion 23 of the lens assumes its "remembered" shaped through the centripetal forces inherent in the lens structure. As an example of the operation of the lens 22, assume that a patient requires plus seventeen (+17) diopters from the lens 22 for distance vision, and plus twenty (+20) diopters for near vision. A significant portion of the required diopters, as much as plus fifteen (+15) reside in or is supplied by the non-accommodating portion 24 of the lens 22, and the accommodating portion 23 is molded to produce plus five (+5) diopters in its normal or "remembered" shape. When this portion 23 is stretched by centrifugal tension from the ciliary body 14 through zonules 21 and capsular bag 16, its curvature flattens and its optical power contribution drops to plus two (+2) diopters. Thus, when the patient views distant objects, the ciliary body 14 is relaxed, the zonules 21 are placed under tension, the capsular bag 16 is stretched, the lens 22 flattens, and the required +17 diopters results. On the other hand, when the patient views near objects, the ciliary body 14 constricts, the tension on zonules 21 is released, and the centripetal forces in the soft polymer portion 23 cause portion 23 to assume its "memory" shape, thereby increasing the contribution of portion 23 to +5 diopters, and the total power of the lens 22 to +20 diopters.

The soft polymer of the molded accommodating portion 23 must be such that the built-in centripetal force can be overcome by the centrifugal force or tension generated by the ciliary body 14, zonules 21, and capsular bag 16, when the ciliary body 14 relaxes. A preferred material for portion 23 is silicone, although other known materials can also be used so long as they meet the required characteristics for IOL implants and are sufficiently soft to meet the force responsive requirement set forth in the foregoing.

Figure 5:
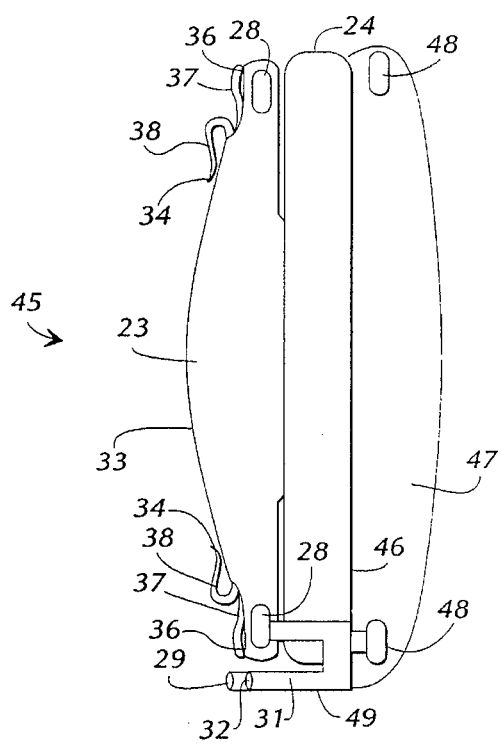
FIG. 5 is an elevation view of another embodiment of the intraocular lens of the invention.

In FIG. 5, there is shown a second embodiment of the lens of the present invention, wherein the posterior portion of the lens is made adjustable. For simplicity, those parts of the lens 45 corresponding to like parts in the lens 22 of FIGS. 3A and 3B have been given the same reference numerals. As can be seen in FIG. 5, lens 45 comprises an accommodating portion 23 and a posterior portion 24 of a fixed focus. On the posterior wall 46 of portion 24 there is attached, as by fusion or cement, an adjustable posterior portion 47 composed of a soft polymer such as silicone. An expansion channel 48 extends 360 degrees around the interior periphery of portion 47 in a manner similar to channel 28 in anterior portion 23, and is connected to access port 29, through valve means 32 and tube 49, which is separate from tube 31. Channel 48 is adapted to receive a viscoelastic material which alters the shape, and hence the focusing power of portion 47. Thus, with the arrangement of FIG. 5, the "fixed" power of the combination of portions 24 and 47, i.e., the posterior portion of the lens may be adjusted before, during, or after implantation. The implantation of lens 45 within the capsular bag 16 is the same as for the lens 22 of FIGS. 3A and 3B.

From the foregoing it can be seen that the lens of the invention, when properly implanted, affords a desired amount of accommodation for the patient while also affording distance vision also. The lens, by being attached to the anterior wall of the capsular bag, undergoes changes in power in much the same way as the crystalline lens of the normal eye, and the forces acting on the lens are the same forces as are characteristic of a normal eye. With the arrangement, it is also possible to fine tune the focusing power of the lens to suit the patient's needs. In the implantation of the lens, very little invasion of the capsular bag is necessary, and possible damage of the ciliary body by direct connection thereto is avoided.

The foregoing has been for the purpose of illustrating the principles and features of the invention as embodied in preferred structures. Numerous changes or variations of structure may occur to workers in the art without departure from the spirit and scope of the invention.

I claim:

1. A lens implant for the eye, wherein the eye has a substantially intact capsulary bag having anterior and posterior walls and a capsulorexis opening with edges in said anterior wall, said implant comprising:
   a first lens portion of a deformable material, said lens portion having a periphery and anterior and posterior surfaces;
   affixing means on said lens portion adjacent said periphery for affixing said first said lens portion to the anterior wall of the capsular bag whereby forces on the anterior wall are transmitted to said lens portion;
   said affixing means comprising a shelf on said lens portion adjacent the periphery thereof, said shelf being coated with a pigmented polymer gel having a fight absorption characteristic, said shelf being adapted to receive and underlie the inner surface of the anterior wall of the capsulary bag adjacent the opening therein.

2. A lens implant as claimed in claim 1, wherein said first lens portion has an anterior periphery and an expansion channel extending around said interior periphery.

3. A lens implant as claimed in claim 2, and further including access means for injection of material into said expansion channel from outside said first lens portion.

4. A lens implant as claimed in claim 1, and further comprising a second lens portion affixed to said posterior surface of said first lens portion.

5. A lens implant as claimed in claim 4, wherein said second lens portion has a fixed focal length.

6. A lens implant as claimed in claim 4, wherein said second lens portion has a variable focal length.

7. A lens implant as claimed in claim 6, in which said second lens portion has an interior periphery with an expansion channel extending around said interior periphery.

8. A lens implant as claimed in claim 7, and further comprising access means for injection of material into said expansion channel from outside of said second lens portion.

9. A lens implant as claimed in claim 4, wherein said second lens portion comprises a first member having a fixed focal length and a second member having a variable focal length.

10. A lens implant as claimed in claim 9, in which said second member has an interior periphery with an expansion channel extending around said interior periphery.

11. A lens implant as claimed in claim 10, and further comprising access means for injection of material into said expansion channel.

12. A lens implant for the eye, wherein the eye has a substantially intact capsulary bag having anterior and posterior walls and a capsulorexis opening with edges in said anterior wall, said implant comprising:
    a first lens portion of a deformable material, said lens portion having a periphery and anterior and posterior surfaces;
    affixing means on said lens portion adjacent said periphery for affixing said first lens portion to the anterior wall of the capsular bag whereby forces on the anterior wall are transmitted to said lens portion;
    said affixing means comprising a flap on said lens portion adjacent the periphery thereof, said flap being adapted to overlie and contact the outer surface of the capsulary bag adjacent the opening therein, said flap being coated with a pigmented polymer gel having a light absorption characteristic.

13. A lens implant as claimed in claim 12, wherein said first lens portion has an interior periphery with an expansion channel extending around said interior periphery.

14. A lens implant as claimed in claim 13, and further including access means for injection of material into said expansion channel from outside said first lens portion.

15. A lens implant as claimed in claim 12, and further comprising a second lens portion affixed to said posterior surface of said first lens portion.

16. A lens implant as claimed in claim 15, wherein said second lens portion has a fixed focal length.

17. A lens implant as claimed in claim 15, wherein said second lens portion has a variable focal length.

18. A lens implant as claimed in claim 17, in which said second lens portion has an interior periphery with an expansion channel extending around said interior periphery.

19. A lens implant as claimed in claim 18, and further comprising access means for injection of material into said expansion channel from outside of said second lens portion.

20. A lens implant as claimed in claim 15, wherein said second lens portion comprises a first member having a fixed focal length and a second member having a variable focal length.

21. A lens implant as claimed in claim 20, in which said second lens portion has an interior periphery with an expansion channel extending around said interior periphery.

22. A lens implant as claimed in claim 21, and further comprising access means for injection of material into said expansion channel.

23. A lens implant for the eye, wherein the eye has a substantially intact capsulary bag having anterior and posterior walls, said implant comprising:

a first lens portion of a deformable material, said lens portion having a periphery and anterior and posterior surfaces;

affixing means on said lens portion adjacent said periphery for affixing said first lens portion to the anterior wall of the capsular bag whereby forces on the anterior wall are transmitted to said lens portion;

said implant further comprising a second lens portion affixed to said posterior surface of said first lens portion, said second lens portion having an interior periphery and a variable focal length with an expansion channel extending around said interior periphery.

24. A lens implant as claimed in claim 23, and further comprising access means for injection of material into said expansion channel from outside of said second lens portion.

25. A lens implant for the eye, wherein the eye has a substantially intact capsulary bag having anterior and posterior walls, said implant comprising:

a first lens portion of a deformable material, said lens portion having a periphery and anterior and posterior surfaces;

affixing means on said lens portion adjacent to said periphery for affixing said first lens portion to the anterior wall of the capsular bag whereby forces on the anterior wall are transmitted to said lens portion;

said implant further comprising a second lens portion affixed to said posterior surface of said first lens portion, said second lens portion having an interior periphery and a first member having a fixed focal length and a second member having a variable focal length with an expansion channel extending around the interior periphery of said second member.

26. A lens implant as claimed in claim 25, and further comprising access means for injection of material into said expansion channel.

27. A lens implant for the eye, wherein the eye has a substantially intact capsulary bag having anterior and posterior walls, each having front and rear surfaces and an opening in the anterior wall, said implant comprising:

a first lens portion of a deformable material, said lens portion having an external periphery and an internal periphery and anterior and posterior surfaces;

a second lens portion having anterior and posterior surfaces and an interior periphery, the interior surface of said second lens portion being affixed to the posterior surface of said first lens portion;

affixing means on said anterior surface of said first lens portion adjacent said external periphery thereof for affixing said first lens portion within the opening in the anterior wall of the capsulary bag, said affixing means comprising means adapted to underlie and contact the rear surface of the anterior wall of the capsulary bag adjacent the opening therein; and means for altering the focal length of said first portion comprising an expansion channel within said first lens portion and extending around the interior periphery thereof.

28. A lens implant as claimed in claim 27, in which said second lens portion has a fixed focal length.

29. A lens implant as claimed in claim 27, and further comprising access means for the injection of viscoelastic material into said expansion channel.

30. A lens implant for the eye, wherein the eye has a substantially intact capsulary bag having anterior and posterior walls, each having front and rear surfaces and an opening in the anterior wall, said implant comprising:

a first lens portion of a deformable material, said lens portion having an external periphery and an internal periphery and anterior and posterior surfaces;

a second lens portion having anterior and posterior surfaces and an interior periphery, the anterior surface of said second lens portion being affixed to the posterior surface of said first lens portion;

affixing means on said anterior surface of said first lens portion adjacent said external periphery thereof for affixing said first lens portion within the opening in the anterior wall of the capsulary bag, said affixing means comprising means adapted to underlie and contact the rear surface of the anterior wall of the capsulary bag adjacent the opening therein; and means for altering the focal length of said second lens portion comprising an expansion channel within said deformable member and extending around the interior periphery thereof.

31. A lens implant as claimed in claim 30, and further comprising access means for the injection and removal of viscoelastic material into said expansion channel within said deformable member.

32. A lens implant for the eye, wherein the eye has a substantially intact capsulary bag having anterior and posterior walls, each having front and rear surfaces and an opening in the anterior wall, said implant comprising:

a first lens portion of a deformable material, said lens portion having an external periphery and an interior periphery and anterior and posterior surfaces;

a second lens portion having anterior and posterior surfaces and an interior periphery, the anterior surface of said second lens portion being affixed to the posterior surface of said first lens portion;

affixing means on said anterior surface of said first lens portion adjacent said external periphery thereof for affixing said first lens portion within the opening in the anterior wall of the capsulary bag, said affixing means comprising means adapted to underlie and contact the rear surface of the anterior wall of the capsulary bag adjacent the opening therein;

means for altering the focal length of said first lens portion comprising an expansion channel extending around the interior periphery of said first lens portion; and means for altering the focal length of said second lens portion.

33. A lens implant as claimed in claim 32, wherein said means for altering the focal length of said second lens portion comprises a second expansion channel extending around the interior periphery of said second lens portion.

34. A lens implant as claimed in claim 33, and further comprising first access means for the injection of material into said expansion channel and second access means for the injection of material into said second expansion channel.

35. A lens implant for the eye, wherein the eye has a substantially intact capsulary bag having anterior and posterior walls and a capsulorexis opening with edges in said anterior wall, said implant comprising:

a first lens portion of a deformable material, said lens portion having an interior periphery and anterior and posterior surfaces;

affixing means on said lens portion adjacent said periphery for affixing said first lens portion to the anterior wall of the capsular bag whereby forces on the anterior wall are transmitted to said lens portion; and said first lens portion having an expansion channel extending around said interior periphery and access means for injection and removal of material into said expansion channel for altering the focal length of said first lens portion.

36. A lens implant for the eye, wherein the eye has a substantially intact capsulary bag having anterior and posterior walls, each having front and rear surfaces and an opening in the anterior wall, said implant comprising:

a first lens portion of a deformable material, said first lens portion having an external periphery and an internal periphery and anterior and posterior surfaces;

a second lens portion having anterior and posterior surfaces and an interior periphery, the anterior surface of said second lens portion being affixed to the posterior surface of said first lens portion;

affixing means on said anterior surface on said first lens portion adjacent said external periphery thereof for affixing said first lens portion within the opening in the anterior wall of the capsulary bag;

means for altering the focal length of said first lens portion comprising an expansion channel within said first lens portion and extending around the internal periphery thereof; and access means for the injection and removal of material into and out of said expansion channel for altering focal length of said first lens portion.

37. A lens implant as defined in claim 36 and further including means for altering the focal length of said second lens portion comprising an expansion channel extending around the interior periphery of said second lens portion with access means for the injection and removal of material into and out of said expansion channel.

38. A method of implanting an accommodating intraocular lens within an eye, wherein the eye has a substantially intact, empty capsulary bag having an opening in the interior wall thereof and the intraocular lens has an interior wall, a periphery, and a deformable portion comprising an expansion channel extending around said periphery with an access means for the injection and removal of a material into and out of said expansion channel for altering the shape and focal length of said intraocular lens, said method comprising the steps of:

inserting a material through said access means into said expansion channel for deforming said intraocular lens into a shape having a non-accommodating shape prior to inserting said lens into capsulary bag;

inserting the intraocular lens into the capsulary bag through the opening therein;

affixing the deformable portion of the lens to the ed capsulary bag defined by the opening; and adjusting the amount of said material through said access means in said channel to attain a desired focal length of said lens.

39. The method of implanting an accommodating intraocular lens as claimed in claim 38, wherein the step of affixing the deformable portion includes the steps of:

forming a shelf on the anterior wall of the lens adjacent the periphery thereof; and positioning the lens within the capsulary bag so that the interior wall of the capsulary bag adjacent the opening therein overlays and contacts the shelf.

40. The method of implanting an accommodating intraocular lens as claimed in claim 39, and further including the steps of:

coating the shelf with a polymer gel; and melting the gel to fuse the capsulary bag to the shelf.

41. The method of implanting an accommodating intraocular lens as claimed in claim 39, wherein the step of forming a shelf includes the steps of forming at least one flap adjacent the shelf.

42. The method of implanting an accommodating lens as claimed in claim 41, and further including the step of overlaying the anterior wall of the capsulary bag adjacent the opening therein with the flap after positioning the lens within a capsulary bag.

43. The method of implanting an accommodating lens as claimed in claim 38, and wherein the lens has a second deformable portion having a periphery with an expansion channel extending around the periphery thereof and an access means for the insertion of material into said expansion channel, including the step of:

deforming the second deformable portion to alter the shape thereof prior to insertion into the capsulary bag.

* * * * *